United States Patent
Mathur et al.

(10) Patent No.: US 6,417,356 B1
(45) Date of Patent: Jul. 9, 2002

(54) STABILIZATION OF VINYLETHER AND VINYL LACTAM FORMULATIONS AGAINST HYDROLYSIS

(75) Inventors: Arvind M. Mathur, Wayne; James A. Dougherty, Kinnelon, both of NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/764,641

(22) Filed: Jan. 18, 2001

(51) Int. Cl.[7] .................. C07B 63/00; C07B 63/02; C07B 63/04; C07D 201/18
(52) U.S. Cl. .................. 540/485; 540/540; 548/401; 548/543; 548/555; 564/305; 564/461; 564/512; 568/582
(58) Field of Search ................. 540/485, 540; 548/401, 543, 555; 568/582

(56) References Cited

PUBLICATIONS

Wolters et al., Chemical Abstracts, vol. 134:57127, 2000.*

* cited by examiner

Primary Examiner—Richard L. Raymond
(74) Attorney, Agent, or Firm—Marilyn J. Maue; William J. Davis; Walter Katz

(57) ABSTRACT

This invention relates to a composition containing (a) a component selected from the group of a mono- or poly-vinyl substituted mono- or poly-ether, a mono- or poly-vinyl substituted lactam, or a mixture thereof contained in an acidic medium and (b) an aliphatic, primary or secondary mono- or poly-amine at a concentration sufficient to adjust the pH of the composition above

16 Claims, 2 Drawing Sheets

STABILIZATION OF VINYLETHER AND VINYL LACTAM FORMULATIONS AGAINST HYDROLYSIS

BACKGROUND OF THE INVENTION

Figure 1A:
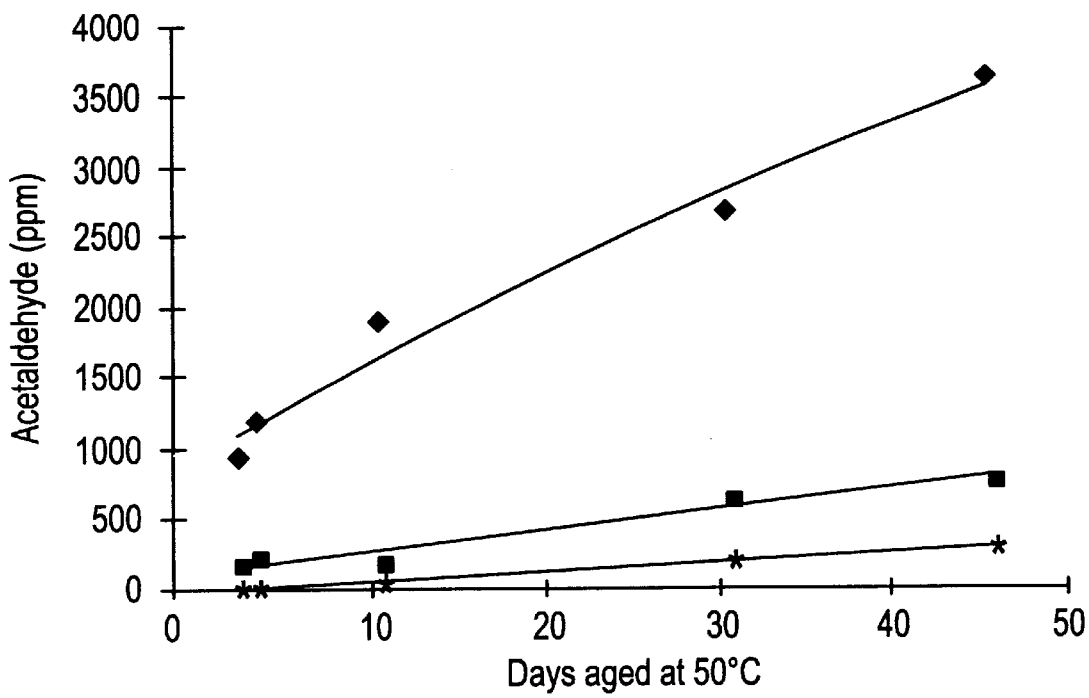

The use of mono- or poly-vinyl substituted mono- or poly-ethers and mono- or poly-vinyl substituted lactams as monomers and comonomrs in polymerization reactions or as crosslinking agents or reactive diluents for UV curable coatings is well known. Since the efficacy of these components depends on the presence and availability of the vinyl moiety, it is important to avoid in situ reactions which result in saturated by-products, such as malodorous acetaldehyde and hydroxylated ethers which significantly lower the reactivity of the vinyl ethers or vinyl lactams for their intended uses. Notwithstanding this difficulty, most formulations involving these vinyl compounds in the above reactions require the presence of acidic components such as, for example silica employed as a leveling agent in coating compositions, oligomers of vinyl esters derived from carboxylic acids which are employed as reactive diluents in UV curable formulations and matrices for acidic pigments or inks. These acidic components in an aqueous atmosphere attack the vinyl groups resulting in the formation of acetaldehyde and hydroxy ether by-products. Obviously, the degree of vinyl degradation depends on the amount of moisture and concentration of acidic components present; however any degree of lower efficacy is undesirable.

By way of illustration, the objectionable side reactions involving monovinyl ethyl ether proceeds as follows.

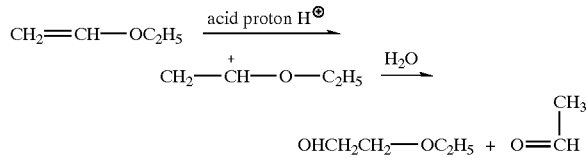

Several solutions designed to minimize the above problem have been advanced and include the use of chemical scavengers to react with and/or to remove the undesirable components as formed or the addition of a highly efficient drying agents, such as KOH or NaOH, to remove traces of moisture. Although somewhat effective, these methods are expensive and introduce extraneous components which do not promote desired reactions of the vinyl groups. Further, several effective scavengers cause objectionable discoloration of the mixtures and formulated products.

Accordingly, it is an object of this invention to provide an economical an commercially viable solution to the above problem by the use of minimal amounts of hydrolysis inhibitor.

Another object is to provide clear and colorless hydrolysis stabilized mixtures using relatively small amounts of stabilizer.

Still another object is to provide a stabilizer for vinyl ether monomers and crosslinking agents which do not interfere with free radical polymerization reactions.

These and other objects of the invention will become apparent from the following description and disclosure.

SUMMARY OF THE INVENTION

The present invention relates to the hydrolysis inhibition of vinyl ethers and vinyl lactams contained in an acidic formulation by the addition of an aliphatic, primary or secondary amine in an amount sufficient to at least neutralize, and preferably to alkalinize, the formulation containing the vinyl component and also to the hydrolysis resistant composition resulting from the mixture of the vinyl component with the instant aliphatic amine compounds.

DETAILED DESCRIPTION OF THE INVENTION

In accordance with this invention there is provided a composition comprising (a) a $C_3$ to $C_{14}$ vinyl compound, such as a mono-, di- or tri-vinyl substituted mono- or poly-ether and/or a mono- or di-vinyl N-vinyl lactam, contained in an acidic formulation and (b) a hydrolysis inhibiting amount of an aliphatic, linear, branched or cyclic mono- or poly-amine wherein at least one amino group is primary or secondary and preferably wherein at least one amino group is a primary amino.

The preferred vinyl ethers are defined by the formula:

$$CH_2=CH-O-(XO)_n-Y(Z)$$

wherein
X is ethylene or propylene;
n has a value of 0 to 5;
Y is $C_2$ to $C_8$ alkylene optionally substituted with a vinyl group and
Z is hydrogen or $-O-CH=CH_2$.
Most preferred of this group are the vinyl ethers wherein n is 2 or 3 and Z is $-O-CH=CH_2$.

The preferred vinyl lactams are N-vinyl pyrrolidones or N-vinyl caprolactams which optionally may have one or two additional vinyl groups substituted on a ring carbon atom.

Acidic formulations in which the vinyl compounds are contained commonly include silica, an unsaturated polyester, an acrylate and/or similar substances providing a source of acidity.

In certain cases, e.g. where crosslinking is intended, the vinyl ether or lactam represents a minor portion of the formulation, typically between about 1 and about 15 wt. %, thus there is a paucity of vinyl moieties which need be shielded against hydrolysis and acidic sites in the formulation exist in correspondingly small amounts, e.g. from about 0.05 and about 15 wt. %. Thus; relatively low concentrations of amine are needed to neutralize or to raise the pH of the formulation to neutral or above 7. Conversely, where a high concentration of the vinyl compound is desired, as for example in 40–80% of vinyl ether is desired for copolymerization, or where 80–95% of the UV Curable vinyl ether is used as a matrix for an ink or pigment, or other uses where the comonomer is in high concentration, a greater amount of the amine is required to prevent hydrolysis. In most cases the concentration of the amine is between about 200 ppm and about 100,000 ppm, preferably between 500–50,000, of the entire composition or is in an amount at least sufficient to provide a neutral or alkaline media.

The amount of amine required to prevent hydrolysis is dependent on several factors; for example the acidity of the vinyl group, the acid strength of the formulation, the basicity of the selected amine and the water content of the composition. Generally between about 0.001 and about 15% amine per vinyl radical is recommended to achieve the goals of this invention.

The following are representative acidic formulations illustrating the wide range of vinyl ether or vinyl lactam concentration.

Formulation 1
UV Curable ink

| Ingredient | Wt. % |
|---|---|
| Yellow pigment | 7.5 |
| RAPI-CURE ® DVE-3 | 28.7 |
| Solsperse 24000 SC/ 22000 mixture** | 1.2 |
| Cyracure 6110 epoxy[3] | 58.6 |
| Degacure K185*** | 4.0 |

Formulation 2
Curable Unsaturated polyester Coating

| Ingredient | Wt. % |
|---|---|
| Hetron 197 G* | 61.5 |
| RAPI-CURE ® DVE-3 | 31.5 |
| MEHQ[2] | 0.1 |
| FC 430 fluorocarbon | 0.9 |
| Irgacure 184[a] | 2.9 |
| Silica (Siloid EDAO) | 3.1 |

Formulation 3
Curable wood sealer

| Ingredient | Wt. % |
|---|---|
| (Ebecryl 3200)[1] | 34.1 |
| RAPI-CU RE DVE-3 | 34.1 |
| Talc | 19.5 |
| CaCO$_3$ | 9.7 |
| Triphenyl sulfonium Hexafluorophosphate | 0.6 |
| Irgacure 184[4] | 2.0 |

Formulation 4
Cross linking composition

| Ingredient | Wt. % |
|---|---|
| Vinyl pyrrolidone | 40.5 |
| Vinyl-3-ethylenepyrrolidone | 0.1 |
| Water | 59.0 |
| t-butyl peroxy pivalate | 0.4 |

Formulation 5 fiber-reinforced plastic application

| Component | Wt. % |
|---|---|
| Unsaturated polyester (POLYLITE-EM 28786 X 3243-88-8) Reichhold Chemicals, NC, USA | 65.0 |
| Styrene | 30.0 |
| RAPI-CURE DVE-3 (ISP) | 5.0 |
| Methyteythylketone peroxide (MEKP) | 1.0 phr |
| Cobalt naphthanate (6% Cobalt) | 0.3 phr |
| Dimethylaniline (DMA) | 0.15 phr |
| (NB: phr = parts per hundred resin) | |

Formulation 6-Coating for Flexible Packaging

| Component | Wt. % |
|---|---|
| RAPI-CURE DVE-3 (ISP) | 80.0 |
| Cellulose acetate Butyrate | 20.0 |
| Cationic photoinitiator UVI-6990 (Union Carbide) | 4 phr |

Legend
*Hetron 197 G is a halogenated flame-retardent, unsaturated polyester resin available from Ashlard Chemical Co.
**Solsperse 22000 is a polymeric hyperdispersant available from Zeneca corp.
***Degacure K-185 is a free radical photoinitiator supplied by Degussa Co.
[1]Ebecryl 3200 is a blend of aromatic & aliphatic acrylated epoxy oligomer available from UCB Radcure Co.
[2]MEHQ is hydroquinone monomethyl ether.
[3]Cyracure 6110 is 3,4-epoxycyclohexylmethy-3,4-epoxycyclohexane carboxylate supplied by Union Carbide
[4]Irgacure 184 is 1-hydroxycyclohexyl phenyl ketone FX-512 is triarylsulfonium hexaflurophosphate cationic photoinitiator from 3M Co.
[5]RAPI-CURE DVE-3 is triethylene glycol divinyl ether The vinyl ether and vinyl lactam compounds of this invention absorb moisture from the atmosphere; hence all formulations containing vinyl compounds contain water.

Standard tests for determining water concentration in formulations are known. For example, the tests for water content in technical grade triethylene glycol divinyl ethyl ether (DVE-3) were performed herein by shaking a 20 gram sample of DVE-3 and 4 grams of deionized water, allowing the mixture to stand for 1 hour and then centrifuging at 3,000 rpm for 5 minutes to ensure complete separation of any suspended water droplets. The separated DVE-3 phase was analyzed to show between 1 and 3% water absorption.

The amino hydrolysis inhibitors of the invention are linear, branched or cyclic aliphatic amines containing from 2 to 8 carbon atoms and from 1 to 6 amino groups where at least one amino is primary or secondary amino, most preferably primary amino. The following formulae A, B and C illustrate preferred amine stabilizers of the present invention.

A. $D[(CH_2)_s]_m NH(H)_p$ wherein D is hydrogen or a primary or secondary amino group; s has a value of from 2 to 8; m has a value of 1 or 2 and p is zero when m is 2 and is 1 when m is 1.

B. $H_2N(CH_2-CH_2NH)_qCH_2-CH_2NH(X)$ wherein q has a value of from 1 to 4 and X is hydrogen or $C_1$ to $C_4$ alkyl and

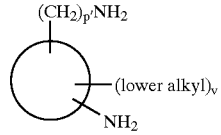

wherein the aliphatic cyclic ring contains 5–6 carbon atoms;
p' has a value of from 1 to 4 and
v has a value of from 0 to 3 and wherein said ring is most preferably saturated.

Of the above compounds, the polyamines are preferred and terminally substituted primary diamines are most preferred.

Representative species of the above amines include dipropyl amine, ethylenediamine, butylenediamine, hexylenediamine, 1,3-diaminopropane, 1,4-diamino-3-methyl butane, 1,4-diamino -3-ethyl butane, 1,4-diamino-2-methylamino butane, 1,4-diamino-3-dimethylamino butane, triethylenetramine, propylenediamine, 1,4-diaminobutane, 1,6-diaminohexane, tripropylenetetramine, 1,8-diaminooctane, 1,7-diamino-3-methyl4-ethyl heptane, 5-amino-2,4-dimethyl-1-cyclopentane, tetraethylenepentamine, tributylenetetramine, 5-amino-2,2,4-trimethyl-1-cyclopentanemethylamine, 6-amino-2,2,5-trimethyl-1-cyclohexane methylamine, 5-amino-2,2,4-triethyl-1-cyclopentane ethylamine and the like.

Having generally described the invention, reference is now had to the examples which provide comparisons of various amino compounds as hydrolysis inhibitors as measured by acetaldehyde increase after a 3 and a 12 day storage period. These examples, as they concern the preferred embodiments of the amine inhibitors of this invention are not to be construed as limiting to the scope of the invention as more properly defined in the claims but rather are presented as comparisons with ineffective amines which are excluded from the present invention.

Examples 1 Through 14

Examination of Hydrolysis by Gas Chromatography (GC) Headspace Analysis

The hydrolysis potential of acidic (3 wt. % silica) formulations containing 10 g of DVE-3, in the headspace of a 20 ml vial was measured by GC analysis in the absence and presence of 1000 ppm of an amine of the present invention and other amine compounds.

Comparisons of amine compounds are as reported in Table 1 below.

TABLE 1

| Example | 1 | 2 | 3 | 4 |
|---|---|---|---|---|
| Stabilizer | None | n-propylamine | Dipropylamine | Tripropylamine |
| Structure | | $CH_3-CH_2-CH_2-NH_2$ | $(CH_3-CH_2-CH_2)_2-NH$ | $(CH_3-CH_2-CH_2)_3-N$ |
| Irritant | | | | ● |
| Acetaldh (3 days), ppm | 914 | 157 | 32 | 970 |
| Acetaldh (12 days), ppm | 1844 | 141 | 169 | 1842 |

| Example | 5 | 6 | 7 |
|---|---|---|---|
| Stabilizer | Ethylenediamine | Triethylamine | 1,3-Diaminopropane |
| Structure | $H_2N-CH_2-CH_2-NH_2$ | $(CH_3-CH_2)_3-N$ | $H_2N-(CH_2)_3-NH_2$ |
| Irritant | | | |
| Acetaldh (3 days), ppm | 5 | 818 | 4 |
| Acetaldh (12 days), ppm | 13 | 1814 | 16 |

| Example | 8 | 9 | 10 |
|---|---|---|---|
| Stabilizer | Triethylenetetramine | 5-amino-2,2,4-trimethyl-1-cyclopentanemethylamine | Aniline |
| Structure | $H_2N-CH_2-CH_2-NH-CH_2-CH_2-NH-CH_2-CH_2-NH_2$ | (cyclopentane structure with CH$_2$NH$_2$, NH$_2$, CH$_3$, CH$_3$, H$_3$C) | (phenyl-NH$_2$) |
| Irritant | | ● | ● |
| Acetaldh (3 days), ppm | 3 | 18 | 614 |
| Acetaldh (12 days), ppm | 96 | 418 | 1618 |

| Example | 11 | 12 |
|---|---|---|
| Stabilizer | 1,8-Diaminonapthalene | 1,2-Phenylenediamine |
| Structure | (naphthalene with two NH$_2$) | (benzene with two NH$_2$) |
| Irritant | ● | ● |
| Acetaldh (3 days), ppm | 582 | 514 |
| Acetaldh (12 days), ppm | 2011 | 1376 |

| Example | 13 | 14 |
|---|---|---|
| Stabilizer | 1,3-Phenylenediamine | 1,4-Phenylenediamine |

TABLE 1-continued

| Structure | (1,3-diaminobenzene) | (1,4-diaminobenzene) |
|---|---|---|
| Irritant | ● | ● |
| Acetaldh (3 days), ppm | 439 | 308 |
| Acetaldh (12 days), ppm | 1567 | 1311 |

Figure 1B:
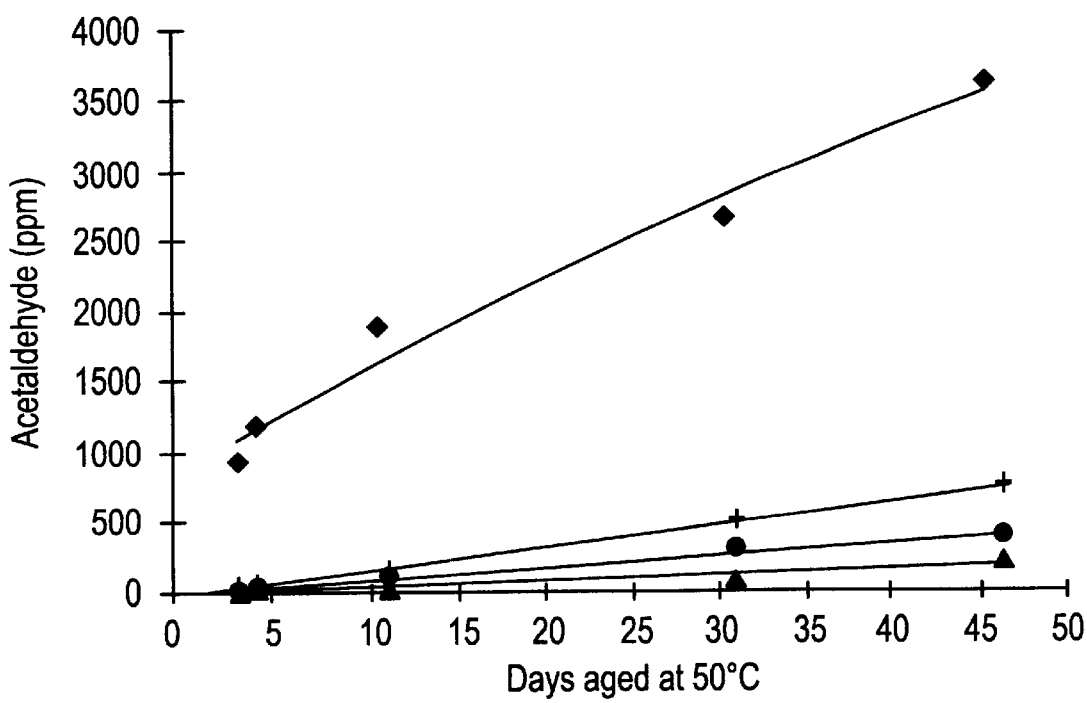
Figure 2:
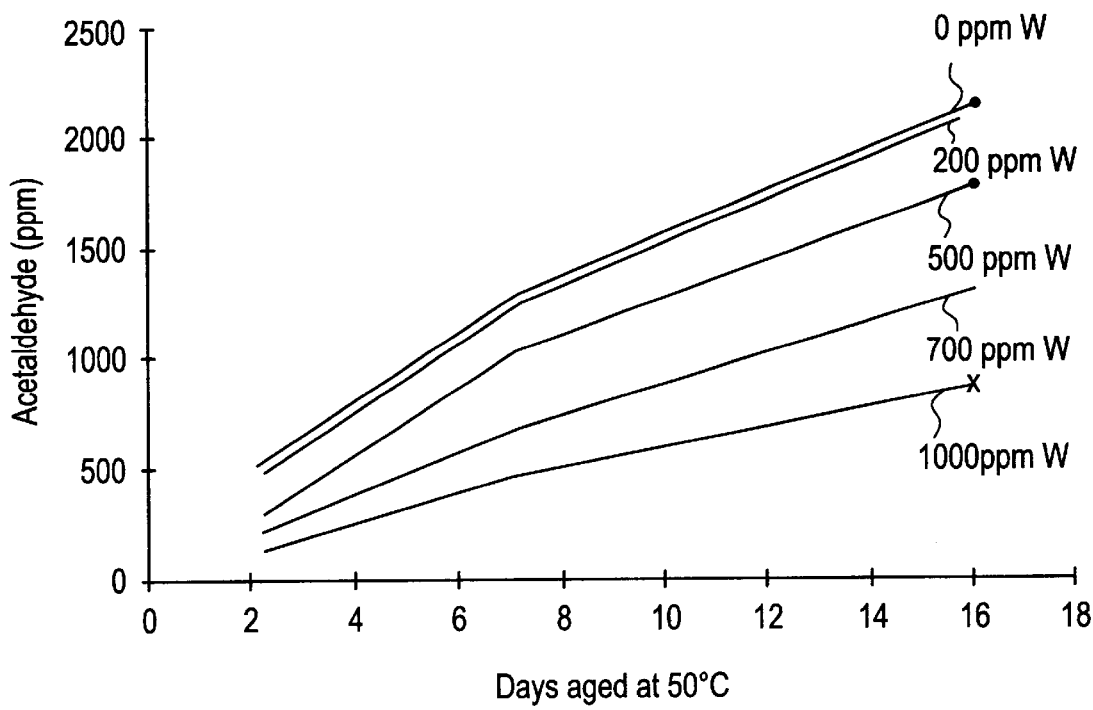

FIGS. 1A and 1B provide graphs of acetaldehyde increase over control containing no amine inhibitor for an extended period up to 45 days. These figures are based on data for DVE-3/silica formulations described above, and containing 1,000 ppm (mass basis) of the following amine hydrolysis inhibitors:

- ◆ control
- ■ n-propylamine
- + dipropyl amine
- Δ ethylenediamine
- ★ 1,3-diaminopropane
- ● triethylenetetraamine FIG. 2 is a graphic representation showing the effects of acetaldehyde increase by varying the concentration of ethylenediamine in a DVE-3/silica formulation similar to Example 1.

Figure 3:
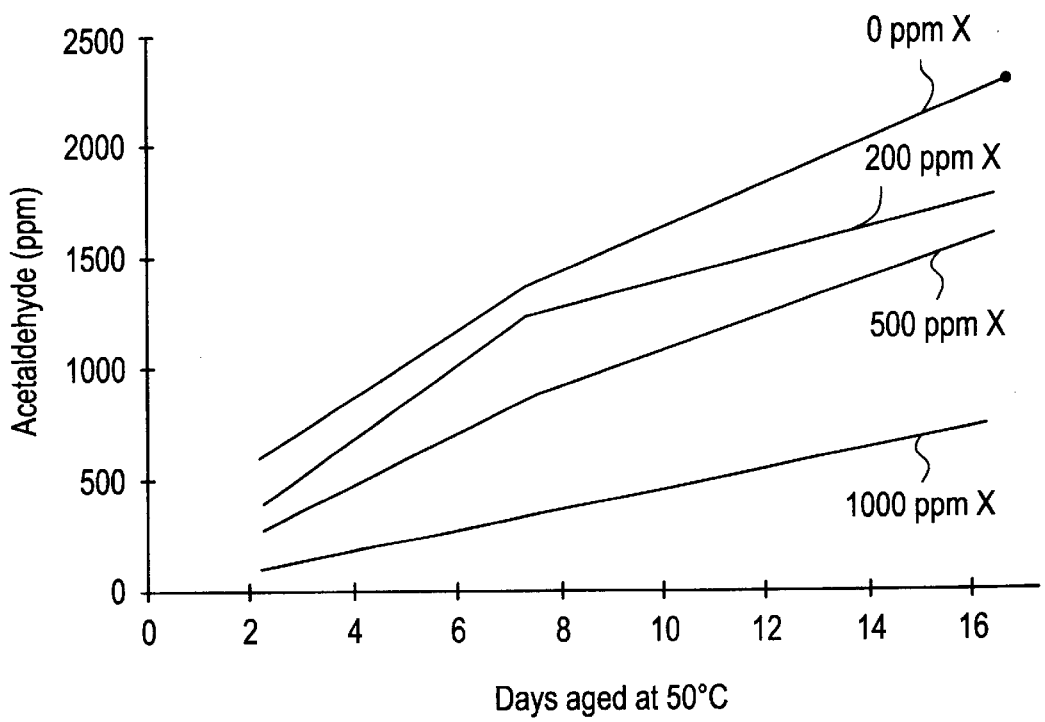

FIG. 3 is a graphic representation showing the effects of acetaldehyde increase with varying amounts of 1,3-diaminopropane in the DVE-3/silica formulation.

It will be understood that many substitutions and alterations in the concentrations of the components reported in the above examples, as well as substitutions of other aliphatic primary or secondary amines, can be made without departing from the scope of this invention

What is claimed is:

1. A hydrolysis inhibiting composition comprising an acidic medium containing (a) a $C_3$ to $C_{14}$ vinyl compound selected from the group consisting of a mono-, di- or tri-vinyl mono- or poly-ether, an N-vinyl lactam optionally containing an additional vinyl group on a ring carbon atom and a mixture thereof and (b) a hydrolysis inhibiting amount of an aliphatic, linear, branched or cyclic mono- or poly-amine wherein at least one amino group is a primary or secondary amino group.

2. The composition of claim 1 wherein at least one amino group of the aliphatic amine is a primary amino group.

3. The composition of claim 2 wherein said amine contains 2 terminal primary amine groups.

4. The composition of claim 3 wherein said amine is ethylenediamine.

5. The composition of claim 2 wherein said amine is 1,3-diamino-propane.

6. The composition of claim 2 wherein said amine is triethylenetetramine.

7. The composition of claim 3 wherein said amine is 5-amino-2,2,4-trimethyl-1-cyclopentane methyl amine.

8. The composition of claim 2 wherein said amine has the formula $$D[(CH_2)_s]_m NH(H)_p$$

wherein D is hydrogen or a primary or secondary amino group; s has a value of from 2 to 8; m has a value of from 1 to 2; and p is zero when m is 2 and is 1 when m is 1.

9. The composition of claim 2 wherein said amine has the formula $H_2N(CH_2CH_2NH)_q CH_2CH_2NH(X)$ wherein q has a value of from 1 to 4 and X is hydrogen or $C_1$ to $C_4$ alkyl.

10. The composition of claim 2 wherein said amine has the formula (cyclic ring with $(CH_2)_{p'}NH_2$, (lower alkyl)$_v$, and $NH_2$ substituents)

wherein the aliphatic cyclic ring contains 4 to 6 carbon atoms;
p' has a value of from 1 to 4;
v has a value of from 0 to 3 and said aliphatic cyclic ring is saturated.

11. The composition of one of claims 1, 2 or 3 wherein said vinyl compound is a monovinyl ether.

12. The composition of one of claims 1, 2 or 3 wherein said vinyl compound is a polyvinyl ether.

13. The composition of one of claims 1, 2 or 3 wherein said ether is triethylene glycol divinyl ether.

14. The composition of claim 1 wherein said N-vinyl lactam is N-vinyl pyrrolidone.

15. The composition of claim 1 wherein said N-vinyl lactam is N-vinyl vinylpyrrolidone.

16. The composition of claim 1 wherein said N-vinyl lactam is N-vinyl caprolactam.

* * * * *